(12) United States Patent
Kim et al.

(10) Patent No.: US 8,440,639 B2
(45) Date of Patent: *May 14, 2013

(54) COMBINATION COMPOSITIONS FOR REDUCING INTRAOCULAR PRESSURE

(75) Inventors: Norman N. Kim, Westford, MA (US); William K. McVicar, Sudbury, MA (US); Thomas G. McCauley, Cambridge, MA (US)

(73) Assignee: Inotek Pharmaceuticals Corporation, Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/051,633

(22) Filed: Mar. 18, 2011

(65) Prior Publication Data

US 2011/0245193 A1    Oct. 6, 2011

Related U.S. Application Data

(60) Provisional application No. 61/315,721, filed on Mar. 19, 2010.

(51) Int. Cl.
| | |
|---|---|
| A61K 31/70 | (2006.01) |
| A61K 31/54 | (2006.01) |
| A61K 31/41 | (2006.01) |
| A61K 31/38 | (2006.01) |
| A01N 43/18 | (2006.01) |
| C07H 19/167 | (2006.01) |
| C07H 19/173 | (2006.01) |
| C07D 285/12 | (2006.01) |
| C07D 285/14 | (2006.01) |
| C07D 417/00 | (2006.01) |
| C07D 513/00 | (2006.01) |
| C07D 327/10 | (2006.01) |
| C07D 339/02 | (2006.01) |
| C07D 341/00 | (2006.01) |
| C07D 409/00 | (2006.01) |
| C07D 411/00 | (2006.01) |
| C07D 495/00 | (2006.01) |
| C07D 497/00 | (2006.01) |
| C07D 285/22 | (2006.01) |
| C07D 285/26 | (2006.01) |

(52) U.S. Cl.
USPC .......... 514/46; 514/222.2; 514/363; 514/432; 536/27.62; 536/27.63; 544/13; 548/141; 549/33

(58) Field of Classification Search .................. None
See application file for complete search history.

(56) References Cited

FOREIGN PATENT DOCUMENTS

| CN | 101010085 | 8/2007 |
|---|---|---|
| WO | 2005/117910 A2 | 12/2005 |
| WO | 2007/064795 A2 | 6/2007 |
| WO | 2010/127210 A1 | 11/2010 |

OTHER PUBLICATIONS

U.S. Appl. No. 12/771,289, First Office Action on the Merits (FAOM), mailed May 23, 2012.*
U.S. Appl. No. 13/051,655, First Office Action on the Merits (FAOM), mailed May 16, 2012.*
U.S. Appl. No. 13/072,349, First Office Action on the Merits (FAOM), mailed Mar. 27, 2012.*
Avila, Marcel Y. et al., "A1-, A2A- and A3-subtype adenosine receptors modulate intraocular pressure in the mouse," British Journal of Pharmacology, vol. 134:241-245 (2001).
Crosson, Craig E., "Adenosine Receptor Activation Modulates Intraocular Pressure in Rabbits," The Journal of Pharmacology and Experimental Therapeutics, vol. 273(1):320-326 (1995).
Crosson, Craig E. et al., "Modulation of Intraocular Pressure by Adenosine Agonists," Journal of Ocular Pharmacology, vol. 10(1):379-383 (1994).
Fredholm, Bertil B. et al., "International Union of Pharmacology. XXV. Nomenclature and Classification of Adenosine Receptors," Pharmacological Reviews, vol. 53(4):527-552 (2001).
Husain, S. et al., "Mechanisms Linking Adenosine A1 Receptors and Extracellular Signal-Regulated Kinase 1/2 Activation in Human Trabecular Meshwork Cells," The Journal of Pharmacology and Experimental Therapeutics, vol. 320(1):258-265 (2007).
Kim, N. et al., "INO-8875, An Adenosine A1 Agonist, in Development for Open-Angle Glaucoma Reduces IOP in Three Rabbit Models," Investigative Ophthalmology & Visual Science, vol. 50, E-Abstract 4061 (2009).
Mincione, Francesco et al., "The Development of Topically Acting Carbonic Anhydrase Inhibitors as Antiglaucoma Agents," Current Pharmaceutical Design, vol. 14:649-654 (2008).
Nell, Peter G. et al., "The Adenosine A1 Receptor and its Ligands," Progress in Medicinal Chemistry, vol. 47:163-201 (2009).
Ralevic, Vera et al., "Receptors for Purines and Pyrimidines," Pharmacological Reviews, vol. 50(3):413-492 (1998).
Stewart, William C., "Perspectives in the medical treatment of glaucoma," Current Opinion in Ophthalmology, vol. 10:99-108 (1999).
Sugrue, Michael F., "Pharmacological and Ocular Hypotensive Properties of Topical Carbonic Anhydrase Inhibitors," Progress in Retinal and Eye Research, vol. 19(1):87-112 (2000).
Tian, Baohe et al., "Effects of Adenosine Agonists on Intraocular Pressure and Aqueous Humor Dynamics in Cynomolgus Monkeys," Exp. Eye Res., vol. 64:979-989 (1997).
International Search Report for Application No. PCT/US2011/029010, dated May 17, 2011.
Chinese Office Action for Application No. 201080018539.X, 9 pages, dated Nov. 2, 2012.

* cited by examiner

*Primary Examiner* — Lawrence E Crane
(74) *Attorney, Agent, or Firm* — Nelson Mullins Riley & Scarborough LLP; Jane E. Remillard, Esq.; Cynthia L. Kanik

(57) ABSTRACT

Provided herein is a pharmaceutical composition or a kit comprising a combination of a carbonic anhydrase inhibitor analog and an adenosine $A_1$ receptor agonist. Also provided herein is a method of reducing intraocular pressure (IOP) in a subject using such a combination or kit. In a particular embodiment, provided herein is a combination of dorzolamide marketed under the brand Trusopt™ and Compound A.

31 Claims, 2 Drawing Sheets

COMBINATION COMPOSITIONS FOR REDUCING INTRAOCULAR PRESSURE

CROSS-REFERENCE TO RELATED APPLICATIONS

This application claims priority to U.S. Provisional Application No. 61/315,721, filed Mar. 19, 2010. The entire contents of the aforementioned application and any patents, patent applications, and references cited throughout this specification are herein incorporated by reference in their entireties.

TECHNICAL FIELD OF THE INVENTION

Provided herein is a pharmaceutical composition or a kit comprising a combination of a carbonic anhydrase inhibitor analog and an adenosine $A_1$ receptor agonist. Also provided herein is a method of reducing intraocular pressure (IOP) in a subject using such a combination or kit. In a particular embodiment, provided herein is a combination of dorzolamide marketed under the brand Trusopt™ and Compound A.

BACKGROUND OF THE INVENTION

Glaucoma refers to a group of optic neuropathies that are characterized by loss of retinal ganglion cells and atrophy of the optic nerve with resultant visual field loss. The disease is the leading cause of irreversible blindness worldwide and the second leading cause of blindness, behind cataracts. Clinical trials have demonstrated that elevated intra ocular pressure (IOP) is a major risk factor for glaucoma, and have validated the role of lowering IOP in the management of glaucoma.

Glaucoma is classified according to three parameters: 1) the underlying cause, i.e., primary (idiopathic) or secondary (associated with some other ocular or systemic conditions); 2) the state of the anterior chamber angle, i.e., open angle (open access of the outflowing aqueous humor to trabecular meshwork) or closed angle (narrow angle; the trabecular meshwork is blocked by apposition of the peripheral iris and the cornea); and 3) chronicity, i.e., acute or chronic. Although secondary forms of glaucoma with clear etiologies do exist (e.g., pseudoexfoliation and pigmentary dispersion), the most common form of glaucoma is primary open angle glaucoma (POAG).

Ocular hypertension (OHT) is a condition in which IOP is elevated but no glaucomatous findings have been observed (Bell, 2005). The Ocular Hypertension Study demonstrated that patients with OHT have an overall risk of 10% over 5 years of developing glaucoma and that this risk can be cut in half by the institution of medical treatment that reduces IOP.

Accordingly, there remains a need for treatment effective against such disorders.

SUMMARY OF THE INVENTION

In a first aspect there is provided an ophthalmic combination comprising i) an adenosine $A_1$ receptor agonist and ii) a carbonic anhydrase inhibitor for use in reducing intraocular pressure in an eye of a subject.

In one embodiment the carbonic anhydrase inhibitor is selected from dorzolamide, brinzolamide or acetazolamide.

In another embodiment the carbonic anhydrase inhibitor is dorzolamide.

In one embodiment the adenosine $A_1$ receptor agonist is selected from a compound of Formula (I)

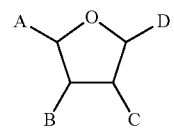

(I)

or pharmaceutically acceptable salts thereof;
wherein
A is $-CH_2OH$, $-(CH_2)_nONO_2$ or $-CH_2OSO_3H$; wherein n=1-6;
B and C are $-OH$;
D is

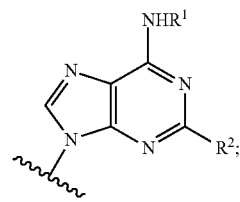

A and B are trans with respect to each other;
B and C are cis with respect to each other;
C and D are cis or trans with respect to each other;
$R^1$ is $-H$, $-C_1$-$C_{10}$ alkyl, -aryl, -3- to 7-membered monocyclic heterocycle, -8- to 12-membered bicyclic heterocycle, $-C_3$-$C_8$ monocyclic cycloalkyl, $-C_3$-$C_8$ monocyclic cycloalkenyl, $-C_8$-$C_{12}$ bicyclic cycloalkyl, $-C_8$-$C_{12}$ bicyclic cycloalkenyl $-(CH_2)_n-(C_3$-$C_8$ monocyclic monocyclic cycloalkyl), $-(CH_2)_n-(C_3$-$C_8$ monocyclic cycloalkenyl), $-(CH_2)_n-(C_8$-$C_{12}$ bicyclic cycloalkyl), $-(CH_2)_n-(C_8$-$C_{12}$ bicyclic cycloalkenyl), or $-(CH_2)_n$-aryl;
$R^2$ is $-H$, halo, $-CN$, $-NHR^4$, $-NHC(O)R^4$, $-NHC(O)OR^4$, $-NHC(O)NHR^4$, $-NHNHC(O)R^4$, $-NHNHC(O)OR^4$, $-NHNHC(O)NHR^4$, or $-NH-N=C(R^6)R^7$;
$R^4$ is $-C_1$-$C_{15}$ alkyl, -aryl, $-(CH_2)_n$-aryl, $-(CH_2)_n$-(3- to 7-membered monocyclic heterocycle), $-(CH_2)_n$-(8- to 12-membered bicyclic heterocycle), $-(CH_2)_n-(C_3$-$C_8$ monocyclic cycloalkyl), $-(CH_2)_n-(C_3$-$C_8$ monocyclic cycloalkenyl), $-(CH_2)_n-(C_8$-$C_{12}$ bicyclic cycloalkyl), $-(CH_2)_n-(C_8$-$C_{12}$ bicyclic cycloalkenyl), $-C\equiv C-(C_1$-$C_{10}$ alkyl) or $-C\equiv C$-aryl;
$R^6$ is $-C_1$-$C_{10}$ alkyl, -aryl, $-(CH_2)_n$-aryl, $-(CH_2)_n$-(3- to 7-membered monocyclic heterocycle), $-(CH_2)_n$-(8- to 12-membered bicyclic heterocycle), $-(CH_2)_n-(C_3$-$C_8$ monocyclic cycloalkyl), $-(CH_2)_n-(C_3$-$C_8$ monocyclic cycloalkenyl), $-(CH_2)_n-(C_8$-$C_{12}$ bicyclic cycloalkyl), $-(CH_2)_n-(C_8$-$C_{12}$ bicyclic cycloalkenyl), $-(CH_2)_n-(C_3$-$C_8$ monocyclic cycloalkenyl), -phenylene-$(CH_2)_n$COOH, or -phenylene-$(CH_2)_n$COO—$(C_1$-$C_{10}$ alkyl); and
$R^7$ is $-H$, $-C_1$-$C_{10}$ alkyl, -aryl, $-(CH_2)_n$-aryl, $-(CH_2)_n$-(3- to 7-membered monocyclic heterocycle), $-(CH_2)_n$-(8- to 12-membered bicyclic heterocycle), $-(CH_2)_n-(C_3$-$C_8$ monocyclic cycloalkyl), $-(CH_2)_n-(C_3$-$C_8$ monocyclic cycloalkenyl), $-(CH_2)_n-(C_8$-$C_{12}$ bicyclic cycloalkenyl) or $-(CH_2)_n-(C_8$-$C_{12}$ bicyclic cycloalkyl) and each n is independently an integer ranging from 1 to 5.

In certain embodiments, the combination includes a compound of formula (I), wherein A is —(CH$_2$)$_n$ONO$_2$;

R$^1$ is -3- to 7-membered monocyclic heterocycle, —C$_3$-C$_8$ monocyclic cycloalkyl, or —C$_8$-C$_{12}$ bicyclic cycloalkyl;

R$^2$ is —H or halo; and

C and D are trans with respect to each other.

In some embodiments, the combination includes a compound of formula (I), wherein R$^1$ is —C$_3$-C$_8$ monocyclic cycloalkyl; and R$^2$ is —H.

In certain embodiments, the combination includes a compound of formula (I), wherein n is 1.

In a further embodiment the compound of Formula I is selected from:

Compound A

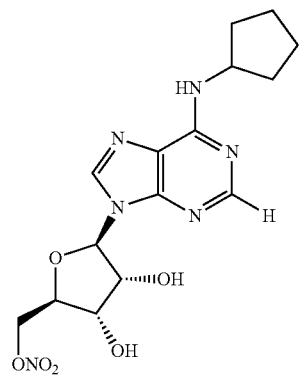

((2R,3S,4R,5R)-5-(6-(cyclopentylamino)-9H-purin-9-yl)-3,4-dihydroxytetrahydrofuran-2-yl)methyl nitrate, Compound B

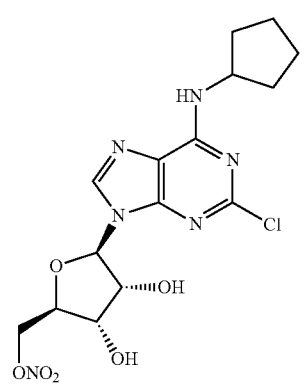

((2R,3S,4R,5R)-5-(2-chloro-6-(cyclopentylamino)-9H-purin-9-yl)-3,4-dihydroxytetrahydrofuran-2-yl)methyl nitrate, Compound C

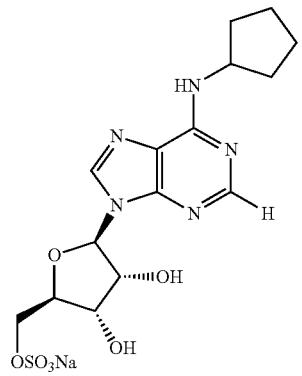

sodium((2R,3S,4R,5R)-5-(6-(cyclopentylamino)-9H-purin-9-yl)-3,4-dihydroxytetrahydrofuran-2-yl)methyl sulfate, Compound D

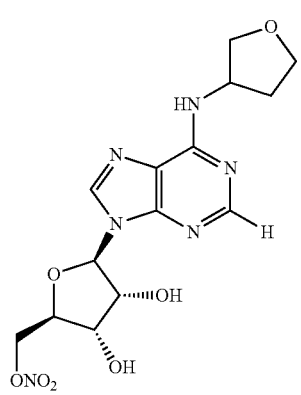

((2R,3S,4R,5R)-3,4-dihydroxy-5-(6-(tetrahydrofuran-3-ylamino)-9H-purin-9-yl)tetrahydrofuran-2-yl)methyl nitrate, Compound E

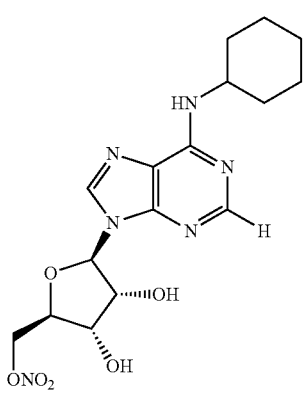

((2R,3S,4R,5R)-5-(6-(cyclohexylamino)-9H-purin-9-yl)-3,4-dihydroxytetrahydrofuran-2-yl)methyl nitrate, Compound F

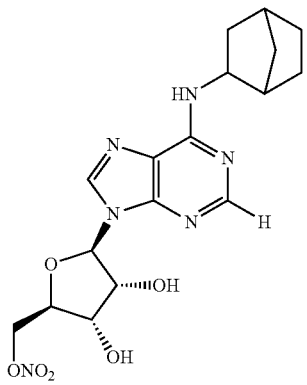

((2R,3S,4R,5R)-5-(6-(bicycle-[2.2.1]-heptan-2-ylamino)-9H-purin-9-yl)-3,4-dihydroxytetrahydrofuran-2-yl)methyl nitrate, Compound G

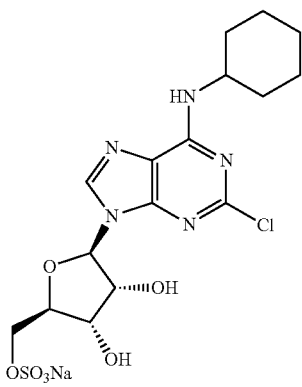

sodium((2R,3S,4R,5R)-5-(2-chloro-6-(cyclohexylamino)-9H-purin-9-yl)-3,4-dihydroxytetrahydrofuran-2-yl)methyl sulfate Compound H

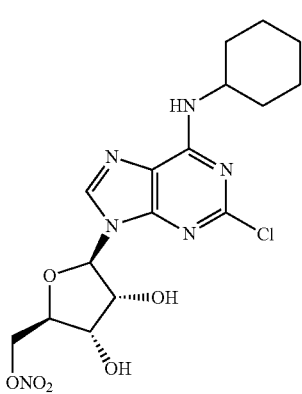

((2R,3S,4R,5R)-5-(2-chloro-6-(cyclohexylamino)-9H-purin-9-yl)-3,4-dihydroxytetrahydrofuran-2-yl)methyl nitrate Compound I

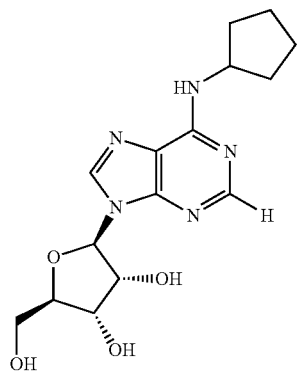

(2R,3R,4S,5R)-2-(6-(cyclopentylamino)-9H-purin-9-yl)-5-(hydroxymethyl)tetrahydrofuran-3,4-diol (N6 Cyclopentyl adenosine (CPA))

Compound J

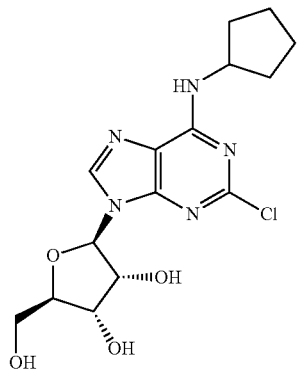

(2R,3R,4S,5R)-2-(2-chloro-6-(cyclopentylamino)-9H-purin-9-yl)-5-(hydroxymethyl)tetrahydrofuran-3,4-diol (N6 Cyclopentyl adenosine (CCPA));
or pharmaceutically acceptable salts thereof.

In a further embodiment the adenosine $A_1$ agonist is Compound A: ((2R,3S,4R,5R)-5-(6-(cyclopentylamino)-9H-purin-9-yl)-3,4-dihydroxytetrahydrofuran-2-yl)methyl nitrate.

In another embodiment the $A_1$ agonist is applied to an eye of the subject simultaneously, separately or sequentially to the application of the carbonic anhydrase inhibitor to the eye of the subject.

In a further embodiment the combination is achieved by applying about 0.05 mg/ml to about 7.0 mg/ml of an $A_1$ agonist with about 2% of a carbonic anhydrase inhibitor to an eye of the subject from 1 to 4 times daily.

In a further embodiment the combination is achieved by applying about 20-700 µg of an $A_1$ agonist to an eye of the subject from 1 to 2 times daily.

In a further embodiment the combination is achieved by applying about 20-350 µg of an $A_1$ agonist to an eye of the subject from 1 to 2 times daily.

In one embodiment the $A_1$ agonist and the carbonic anhydrase inhibitor are administered topically as one or more eye drops to the eye of the subject.

In a further aspect there is provided a method of reducing IOP and associated diseases and conditions caused by elevated IOP in a subject by administering an effective amount of a combination as defined above to an affected eye of the subject.

In one embodiment the diseases and conditions caused by elevated IOP in a human are selected from the group consisting of normal-tension glaucoma, OHT, and POAG.

In a further aspect there is provided a kit comprising i) an adenosine $A_1$ receptor agonist and ii) a carbonic anhydrase inhibitor for use in reducing intraocular pressure in an eye of a subject.

In one embodiment of the kit the carbonic anhydrase inhibitor is selected from dorzolamide, brinzolamide or acetazolamide.

In another embodiment of the kit the carbonic anhydrase inhibitor is dorzolamide.

In a further embodiment of the kit the adenosine $A_1$ receptor agonist is selected from a compound of Formula (I)

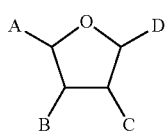

(I)

or pharmaceutically acceptable salts thereof;
wherein
A is —$CH_2OH$, —$(CH_2)_nONO_2$ or —$CH_2OSO_3H$; wherein n=1-6;
B and C are —OH;
D is

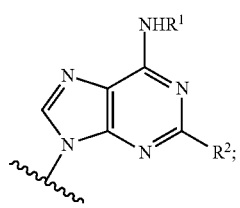

A and B are trans with respect to each other;
B and C are cis with respect to each other;
C and D are cis or trans with respect to each other;
$R^1$ is —H, —$C_1$-$C_{10}$ alkyl, -aryl, -3- to 7-membered monocyclic heterocycle, -8- to 12-membered bicyclic heterocycle, —$C_3$-$C_8$ monocyclic cycloalkyl, —$C_3$-$C_8$ monocyclic cycloalkenyl, —$C_8$-$C_{12}$ bicyclic cycloalkyl, —$C_8$-$C_{12}$ bicyclic cycloalkenyl —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), or —$(CH_2)_n$-aryl;
$R^2$ is —H, halo, —CN, —$NHR^4$, —$NHC(O)R^4$, —$NHC(O)OR^4$, —$NHC(O)NHR^4$, —$NHNHC(O)R^4$, —$NHNHC(O)OR^4$, —$NHNHC(O)NHR^4$, or —NH—N=C($R^6$)$R^7$;
$R^4$ is —$C_1$-$C_{15}$ alkyl, -aryl, —$(CH_2)_n$-aryl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —C≡C—($C_1$-$C_{10}$ alkyl) or —C≡C-aryl;
$R^6$ is —$C_1$-$C_{10}$ alkyl, -aryl, —$(CH_2)_n$-aryl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$—($C_3$-$C_8$ monocyclic cycloalkenyl), -phenylene-$(CH_2)_n$COOH, or -phenylene-$(CH_2)_n$COO—($C_1$-$C_{10}$ alkyl); and
$R^7$ is —H, —$C_1$-$C_{10}$ alkyl, -aryl, —$(CH_2)_n$-aryl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkenyl) or —$(CH_2)_n$—($C_8$-$C_{12}$ bicyclic cycloalkyl) and each n is independently an integer ranging from 1 to 5.

In another embodiment of the kit the compound of Formula I is selected from:

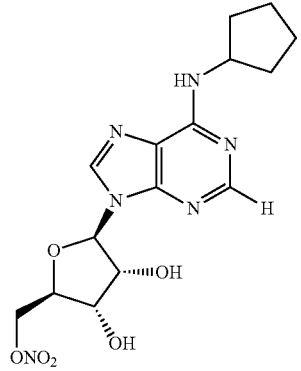

Compound A ((2R,3S,4R,5R)-5-(6-(cyclopentylamino)-9H-purin-9-yl)-3,4-dihydroxytetrahydrofuran-2-yl)methyl nitrate,

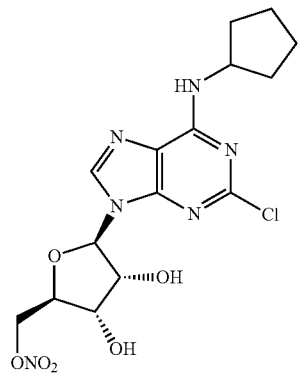

Compound B ((2R,3S,4R,5R)-5-(2-chloro-6-(cyclopentylamino)-9H-purin-9-yl)-3,4-dihydroxytetrahydrofuran-2-yl)methyl nitrate, Compound C

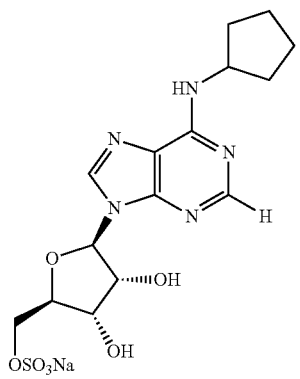

sodium((2R,3S,4R,5R)-5-(6-(cyclopentylamino)-9H-purin-9-yl)-3,4-dihydroxytetrahydrofuran-2-yl)methyl sulfate, Compound D

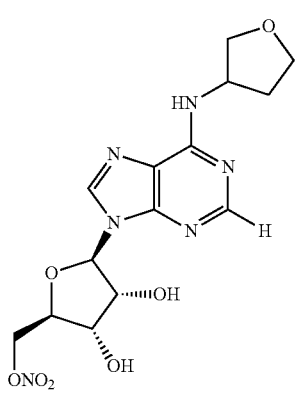

((2R,3S,4R,5R)-3,4-dihydroxy-5-(6-(tetrahydrofuran-3-ylamino)-9H-purin-9-yl)tetrahydrofuran-2-yl)methyl nitrate, Compound E

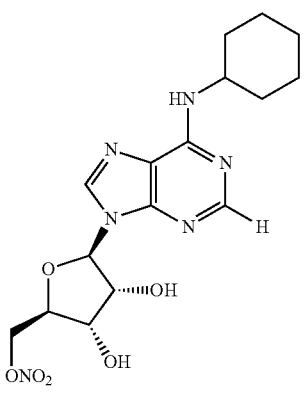

((2R,3S,4R,5R)-5-(6-(cyclohexylamino)-9H-purin-9-yl)-3,4-dihydroxytetrahydrofuran-2-yl)methyl nitrate, Compound F

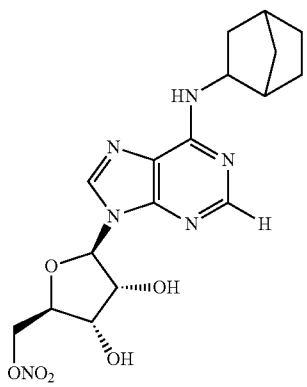

((2R,3S,4R,5R)-5-(6-(bicycle-[2.2.1]-heptan-2-ylamino)-9H-purin-9-yl)-3,4-dihydroxytetrahydrofuran-2-yl)methyl nitrate, Compound G

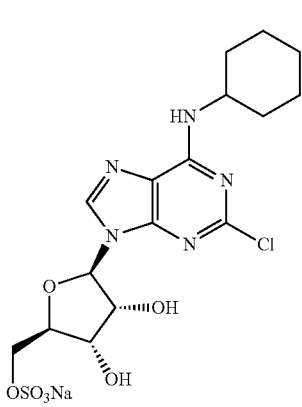

sodium((2R,3S,4R,5R)-5-(2-chloro-6-(cyclohexylamino)-9H-purin-9-yl)-3,4-dihydroxytetrahydrofuran-2-yl)methyl sulfate, and Compound H

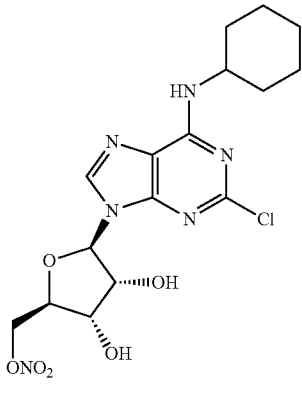

((2R,3S,4R,5R)-5-(2-chloro-6-(cyclohexylamino)-9H-purin-9-yl)-3,4-dihydroxytetrahydrofuran-2-yl)methyl nitrate

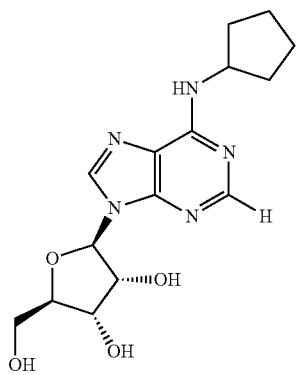

Compound I (2R,3R,4S,5R)-2-(6-(cyclopentylamino)-9H-purin-9-yl)-5-(hydroxymethyl)tetrahydrofuran-3,4-diol (N6 Cyclopentyl adenosine (CPA))

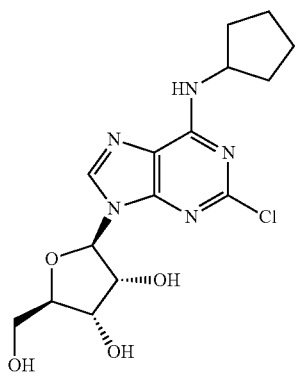

Compound J (2R,3R,4S,5R)-2-(2-chloro-6-(cyclopentylamino)-9H-purin-9-yl)-5-(hydroxymethyl)tetrahydrofuran-3,4-diol (N6 Cyclopentyl adenosine (CCPA));

or pharmaceutically acceptable salts thereof.

In another embodiment of the kit the adenosine $A_1$ agonist is Compound A, ((2R,3S,4R,5R)-5-(6-(cyclopentylamino)-9H-purin-9-yl)-3,4-dihydroxytetrahydrofuran-2-yl)methyl nitrate or a pharmaceutically acceptable salt thereof.

In some embodiments, the ophthalmic combination includes ((2R,3S,4R,5R)-5-(6-(cyclopentylamino)-9H-purin-9-yl)-3,4-dihydroxytetrahydrofuran-2-yl)methyl nitrate and dorzolamide or pharmaceutically acceptable salts thereof, for use in reducing intraocular pressure in an eye of a subject.

In another aspect, the invention provides a method of treating an eye disorder in a subject, comprising administering to an eye of the subject, an effective amount of an ophthalmic combination comprising a compound of formula (I) and a carbonic anhydrase inhibitor or pharmaceutically acceptable salts thereof.

In certain embodiments, the method of treating an eye disorder in a subject, includes administering to an eye of the subject, an effective amount of an ophthalmic combination comprising ((2R,3S,4R,5R)-5-(6-(cyclopentylamino)-9H-purin-9-yl)-3,4-dihydroxytetrahydrofuran-2-yl)methyl nitrate and dorzolamide or pharmaceutically acceptable salts thereof.

In various embodiments, the method includes the eye disorder selected from glaucoma, elevated intraocular pressure and ocular hypertension.

In yet another aspect, the invention provides a use of the combination of a carbonic anhydrase inhibitor and an adenosine $A_1$ receptor agonist for the manufacture of a medicament for treating an eye disorder in a subject.

In some embodiments of the use, the eye disorder is selected from glaucoma, elevated intraocular pressure and ocular hypertension.

In another aspect, the invention provides an ophthalmic pharmaceutical composition including dorzolamide, an adenosine $A_1$ receptor agonist, and a pharmaceutically acceptable vehicle or excipient.

In certain embodiments of the pharmaceutical composition, the pharmaceutically acceptable vehicle or excipient is selected from the group consisting of: ophthalmologically acceptable preservatives, surfactants, viscosity enhancers, penetration enhancers, gelling agents, hydrophobic bases, vehicles, buffers, sodium chloride, and water.

The foregoing brief summary broadly describes the features and technical advantages of certain embodiments of the present invention. Further technical advantages will be described in the detailed description of the invention that follows. Novel features which are believed to be characteristic of the invention will be better understood from the detailed description of the invention when considered in connection with any accompanying figures and examples. However, the figures and examples provided herein are intended to help illustrate the invention or assist with developing an understanding of the invention, and are not intended to be definitions of the invention's scope.

DETAILED DESCRIPTION OF THE INVENTION

Figure 1:
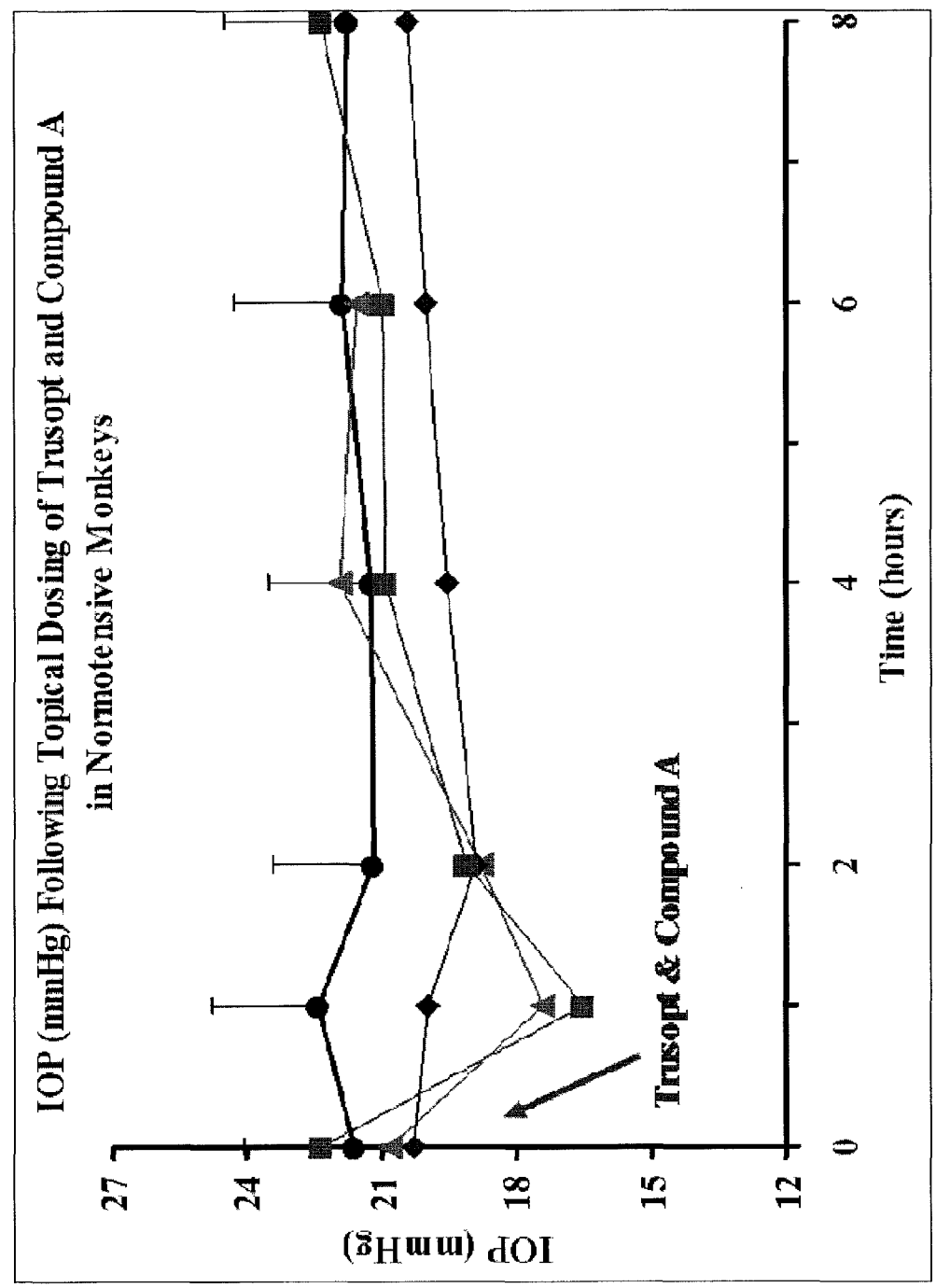
FIG. 1: shows a plot over 8 hrs of the reduction in IOP (mmHg) in normotensive monkeys following ocular dosing of 100 mcg of Compound A alone at 0 hrs, and ocular dosing of a carbonic anhydrase inhibitor (Trusopt, 2%) alone at 0 hrs compared to the reduction in IOP following ocular dosing of both 100 mcg of Compound A and a carbonic anhydrase inhibitor (Trusopt, 2%) at 0 hrs.

Dorzolamide has been used as a topical ophthalmic medication for controlling the progression of open-angle glaucoma or ocular hypertension by reducing intraocular pressure. It is thought that inhibition of carbonic anhydrase II in the ciliary processes of the eye decreases aqueous humor secretion, by slowing the formation of bicarbonate ions with subsequent reduction in sodium and fluid transport. Carbonic anhydrase inhibitors, such as, for example, dorzolamide, can be prepared by using synthetic procedures described in U.S. Pat. Nos. 7,576,122; 7,563,816; 7,528,163; 7,494,983; 7,279,490 and 6,864,383, the disclosures of which are incorporated herein in its entirety.

Dorzolamide is a carbonic anhydrase II inhibitor and has the following chemical structure:

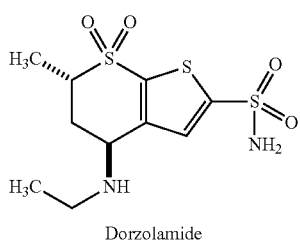 [SMILES: CCN[C@H]1C[C@H](C)S(=O)(=O)c2sc(S(N)(=O)=O)cc21]

Dorzolamide

Adenosine is a purine nucleoside that modulates many physiologic processes. Cellular signaling by adenosine occurs through four adenosine receptor subtypes: $A_1$, $A_{2A}$, $A_{2B}$, and $A_3$ as reported by Ralevic and Burnstock (Pharmacol Rev. 50:413-492, 1988) and Fredholm B B et al (Pharmacol Rev. 53:527-552, 2001). In the eye, adenosine $A_1$ receptor agonists lower IOP in mice, rabbits and monkeys (Tian B et al. Exp Eye Res. 64:979-989, 1997; Crosson C E. J Pharmacol Exp Ther. 273: 320-326, 1995; and Avila M Y et al. Br J Pharmacol. 134:241-245, 2001). While other publications have noted that adenosine $A_1$ receptor agonists in the eye target the conventional outflow pathway via the trabecular meshwork (Husain S et al. J Pharmacol Exp Ther. 320: 258-265, 2007), reduction of IOP via other pathways has not been excluded.

Clinical studies with adenosine $A_1$ receptor agonists have been conducted. These studies have been described in co-pending applications, U.S. Ser. Nos. 61/219,990 and 61/174,655. Clinically significant reduction of intraocular pressure using an adenosine $A_1$ receptor agonist in human subjects having POAG or OHT have been demonstrated. The specifications of U.S. Ser. Nos. 61/219,990 and 61/174,655 are herein incorporated in their entirety as if individually set forth.

Compound A is an adenosine $A_1$ receptor agonist and has the structure:

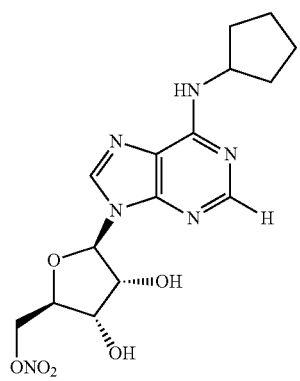

((2R,3S,4R,5R)-5-(6-(cyclopentylamino)-9H-purin-9-yl)-3,4-dihydroxytetrahydrofuran-2-yl)methyl nitrate.

Provided herein is a combination of therapeutic agents and administration of the combination of agents to treat eye disorders such as, for example, glaucoma, elevated intraocular pressure or ocular hypertension. As used herein, a "combination of agents" and similar terms refer to a combination of two types of agents: (1) a carbonic anhydrase inhibitor, such as, for example, dorzolamide and/or pharmacologically active metabolites, salts, solvates and racemates of dorzolamide and (2) an adenosine $A_1$ receptor agonist, such as, for example, compound A, and/or pharmacologically active metabolites, salts, solvates and racemates of compound A. Pharmacologically active metabolites include those that are inactive but converted into pharmacologically active forms in the body after administration.

Embodiments of the present invention provide combinations useful for treating reducing and controlling normal or elevated intraocular pressure (IOP) and/or treating glaucoma.

In one embodiment, provided herein is an ophthalmic combination or kit for use in reducing intraocular pressure, comprising i) an adenosine $A_1$ receptor agonist and ii) a carbonic anhydrase inhibitor for use in reducing intraocular pressure in an eye of a subject.

In one embodiment, the carbonic anhydrase inhibitor is selected from dorzolamide, brinzolamide or acetazolamide. In another embodiment the carbonic anhydrase inhibitor is dorzolamide. In another embodiment provided herein the $A_1$ agonist is Compound A. In another embodiment, provided herein is a method of treating normal-tension glaucoma, comprising administering to an affected eye of a subject an effective amount of a combination of Compound A and dorzolamide. In another embodiment, provided herein is a method of treating OHT, comprising administering to an affected eye of a subject an effective amount of a combination of Compound A and dorzolamide. In another embodiment, provided herein is a method of treating POAG, comprising administering to an affected eye of a subject an effective amount of a combination of Compound A and dorzolamide. In one embodiment of the combination, about 0.05 mg/ml to about 7.0 mg/ml of Compound A is applied to an affected eye of a subject from 1 to 4 times daily. In one embodiment, about 20-700 µg of Compound A is applied to an affected eye of a subject from 1 to 4 times daily. In one embodiment, about 20-350 µg of Compound A is applied to an affected eye of a subject from 1 to 4 times daily. The Compound A can be administered in drops, e.g., 1 to 2 drops. In one embodiment about 2% carbonic anhydrase inhibitor is applied to an affected eye. In one embodiment the subject is a human.

It is recognized that compounds of Formula I can contain one or more chiral centers. This invention contemplates all enantiomers, diastereomers, and mixtures of Formulae I thereof.

Furthermore, certain embodiments of the present invention comprise pharmaceutically acceptable salts of compounds according to Formula I. Pharmaceutically acceptable salts comprise, but are not limited to, soluble or dispersible forms of compounds according to Formula I that are suitable for treatment of disease without undue undesirable effects such as allergic reactions or toxicity. Representative pharmaceutically acceptable salts include, but are not limited to, acid addition salts such as acetate, citrate, benzoate, lactate, or phosphate and basic addition salts such as lithium, sodium, potassium, or aluminum.

DEFINITIONS

As used herein, the term "$A_1$ agonist" refers to an $A_1$ agonist that has an affinity to the $A_1$ receptor while simultaneously having a lower affinity for the $A_2$ and $A_3$ adenosine receptors. Compounds A to J as described herein have affinities to the $A_1$ receptor considerably greater than their respective affinities to the $A_{2A}$ and $A_3$ receptors. The $A_1$ selectivity data for compounds A to J is summarized in the Table below.

| Compound | $A_1$ (Ki (nm)) POTENCY | $A_1 > A_{2A}$ SELECTIVITY [$KiA_2$(nm)/ $KiA_1$(nm)] | $A_1 > A_3$ SELECTIVITY [$KiA_3$(nm)/ $KiA_1$(nm)] |
|---|---|---|---|
| Compound A | 0.97 | 4837 | 725 |
| Compound B | 2.63 | 1593 | 195 |
| Compound C | 4.05 | 2250 | 251 |
| Compound D | 10.6 | >9434 | 202 |
| Compound E | 1.32 | 878 | 1098 |
| Compound F | 1.47 | 3945 | 260 |
| Compound G | 1.36 | 200 | 130 |
| Compound H | 8 | 192 | 167 |
| Compound I | 2.3 | 345 | 31.3 |
| Compound J | 0.83 | 2735 | 50 |

The term "$C_1$-$C_{15}$ alkyl" as used herein refers to a straight or branched chain, saturated hydrocarbon having from 1 to 15 carbon atoms. Representative $C_1$-$C_{15}$ alkyl groups include, but are not limited to methyl, ethyl, propyl, isopropyl, butyl, sec-butyl, tert-buty, pentyl, isopentyl, neopentyl, hexyl, isohexyl, neohexyl, heptyl, isoheptyl, neoheptyl, octyl, isooctyl, neooctyl, nonyl, isononyl, neononyl, decyl, isodecyl, neodecyl, undecyl, dodecyl, tridecyl, tetradecyl and pentadecyl. In one embodiment, the $C_1$-$C_{15}$ alkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_1$-$C_{15}$ alkyl is unsubstituted.

The term "$C_1$-$C_{10}$ alkyl" as used herein refers to a straight or branched chain, saturated hydrocarbon having from 1 to 10 carbon atoms. Representative $C_1$-$C_{10}$ alkyl groups include, but are not limited to methyl, ethyl, propyl, isopropyl, butyl, sec-butyl, tert-butyl, pentyl, isopentyl, neopentyl, hexyl, isohexyl, neohexyl, heptyl, isoheptyl, neoheptyl, octyl, isooctyl, neooctyl, nonyl, isononyl, neononyl, decyl, isodecyl and neodecyl. In one embodiment, the $C_1$-$C_{10}$ alkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_1$-$C_{10}$ alkyl is unsubstituted.

The term "$C_1$-$C_6$ alkyl" as used herein refers to a straight or branched chain; saturated hydrocarbon having from 1 to 6 carbon atoms. Representative $C_1$-$C_6$ alkyl groups include, but are not limited to methyl, ethyl, propyl, isopropyl, butyl, sec-butyl, tert-buty, pentyl, isopentyl, neopentyl, hexyl, isohexyl, and neohexyl. Unless indicated, the C1-C6 alkyl is unsubstituted.

The term "aryl" as used herein refers to a phenyl group or a naphthyl group. In one embodiment, the aryl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the aryl is unsubstituted.

The term "$C_3$-$C_8$ monocyclic cycloalkyl" as used herein is a 3-, 4-, 5-, 6-, 7- or 8-membered saturated non-aromatic monocyclic cycloalkyl ring. Representative $C_3$-$C_8$ monocyclic cycloalkyl groups include, but are not limited to, cyclopropyl, cyclobutyl, cyclopentyl, cyclohexyl, cycloheptyl and cyclooctyl. In one embodiment, the $C_3$-$C_8$ monocyclic cycloalkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_3$-$C_8$ monocyclic cycloalkyl is unsubstituted.

The term "$C_3$-$C_8$ monocyclic cycloalkenyl" as used herein is a 3-, 4-, 5-, 6-, 7- or 8-membered non-aromatic monocyclic carbocyclic ring having at least one endocyclic double bond, but which is not aromatic. It is to be understood that when any two groups, together with the carbon atom to which they are attached form a $C_3$-$C_8$ monocyclic cycloalkenyl group, the carbon atom to which the two groups are attached remains tetravalent. Representative $C_3$-$C_8$ monocyclic cycloalkenyl groups include, but are not limited to, cyclopropenyl, cyclobutenyl, 1,3-cyclobutadienyl, cyclopentenyl, 1,3-cyclopentadienyl, cyclohexenyl, 1,3-cyclohexadienyl, cycloheptenyl, 1,3-cycloheptadienyl, 1,4-cycloheptadienyl, -1,3,5-cycloheptatrienyl, cyclooctenyl, 1,3-cyclooctadienyl, 1,4-cyclooctadienyl, -1,3,5-cyclooctatrienyl. In one embodiment, the $C_3$-$C_8$ monocyclic cycloalkenyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_3$-$C_8$ monocyclic cycloalkenyl is unsubstituted.

The term "$C_8$-$C_{12}$ bicyclic cycloalkyl" as used herein is a 8-, 9-, 10-, 11- or 12-membered saturated, non-aromatic bicyclic cycloalkyl ring system. Representative $C_8$-$C_{12}$ bicyclic cycloalkyl groups include, but are not limited to, decahydronaphthalene, octahydroindene, decahydrobenzocycloheptene, and dodecahydroheptalene. In one embodiment, the $C_8$-$C_{12}$ bicyclic cycloalkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_8$-$C_{12}$ bicyclic cycloalkyl is unsubstituted.

The term "$C_8$-$C_{12}$ bicyclic cycloalkenyl" as used herein is a 8-, 9-, 10-, 11- or 12-membered non-aromatic bicyclic cycloalkyl ring system, having at least one endocyclic double bond. It is to be understood that when any two groups, together with the carbon atom to which they are attached form a $C_8$-$C_{12}$ bicyclic cycloalkenyl group, the carbon atom to which the two groups are attached remains tetravalent. Representative $C_8$-$C_{12}$ bicyclic cycloalkenyl groups include, but are not limited to, octahydronaphthalene, hexahydronaphthalene, hexahydroindene, tetrahydroindene, octahydrobenzocycloheptene, hexahydrobenzocycloheptene, tetrahydrobenzocycloheptene, decahydroheptalene, octahydroheptalene, hexahydroheptalene, and tetrahydroheptalene. In one embodiment, the $C_8$-$C_{12}$ bicyclic cycloalkyl group is substituted with one or more of the following groups: -halo, -0-($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_8$-$C_{12}$ bicyclic cycloalkenyl is unsubstituted.

The term "effective amount" as used herein refers to an amount of a selective adenosine Al agonist that is effective for: (i) treating or preventing elevated IOP; or (ii) reducing IOP in a human.

The term "halo" as used herein refers to —F, —Cl, —Br or —I.

The term "3- to 7-membered monocyclic heterocycle" refers to: (i) a 3- or 4-membered non-aromatic monocyclic cycloalkyl in which 1 of the ring carbon atoms has been replaced with an N, O or S atom; or (ii) a 5-, 6-, or 7-membered aromatic or non-aromatic monocyclic cycloalkyl in which 1-4 of the ring carbon atoms have been independently replaced with a N, O or S atom. The non-aromatic 3- to 7-membered monocyclic heterocycles can be attached via a ring nitrogen, sulfur, or carbon atom. The aromatic 3- to 7-membered monocyclic heterocycles are attached via a ring carbon atom. Representative examples of a 3- to 7-membered monocyclic heterocycle group include, but are not limited to furanyl, furazanyl, imidazolidinyl, imidazolinyl, imidazolyl, isothiazolyl, isoxazolyl, morpholinyl, oxadiazolyl, oxazolidinyl, oxazolyl, oxazolidinyl, pyrimidinyl, phenanthridinyl, phenanthrolinyl, piperazinyl, piperidinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, quinuclidinyl, tetrahydrofuranyl, thiadiazinyl, thiadiazolyl, thienyl, thienothiazolyl, thienooxazolyl, thienoimidazolyl, thiomorpholinyl, thiophenyl, triazinyl, triazolyl, In one embodiment, the 3- to 7-membered monocyclic heterocycle group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the 3- to 7-membered monocyclic heterocycle is unsubstituted.

The term "8- to 12-membered bicyclic heterocycle" refers to a bicyclic 8- to 12-membered aromatic or non-aromatic bicyclic cycloalkyl in which one or both of the of the rings of the bicyclic ring system have 1-4 of its ring carbon atoms independently replaced with a N, O or S atom. Included in this class are 3- to 7-membered monocyclic heterocycles that are fused to a benzene ring. A non-aromatic ring of an 8- to 12-membered monocyclic heterocycle is attached via a ring nitrogen, sulfur, or carbon atom. An aromatic 8- to 12-membered monocyclic heterocycles are attached via a ring carbon atom. Examples of 8- to 12-membered bicyclic heterocycles include, but are not limited to, benzimidazolyl, benzofuranyl, benzothiofuranyl, benzothiophenyl, benzoxazolyl, benzthiazolyl, benztriazolyl, benztetrzolyl, benzisoxazolyl, benzisothiazolyl, benzimidazolinyl, cinnolinyl, decahydroquinolinyl, 1H-indazolyl, indolenyl, indolinyl, indolizinyl, indolyl, isobenzofuranyl, isoindazolyl, isoindolyl, isoindolinyl, isoquinolinyl, naphthyridinyl, octahydroisoquinolinyl, phthalazinyl, pteridinyl, purinyl, quinoxalinyl, tetrahydroisoquinolinyl, tetrahydroquinolinyl, and xanthenyl. In one embodiment, each ring of a the -8- to 12-membered bicyclic heterocycle group can substituted with one or more of the following groups: -halo, —O—($C_1$-$C_6$ alkyl), —OH, —CN, —COOR', —OC(O)R', —N(R')$_2$, —NHC(O)R'. or —C(O)NHR' groups wherein each R' is independently —H or unsubstituted —$C_1$-$C_6$ alkyl. Unless indicated, the 8- to 12-membered bicyclic heterocycle is unsubstituted.

The phrase "pharmaceutically acceptable salt," as used herein, is a salt of an acid and a basic nitrogen atom of a purine compound. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The pharmaceutically acceptable salt can also be a camphorsulfonate salt. The term "pharmaceutically acceptable salt" also refers to a salt of a purine compound having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like. The term "pharmaceutically acceptable salt" also includes a hydrate of a purine compound. Some chemical structures herein are depicted using bold and dashed lines to represent chemical bonds. These bold and dashed lines depict absolute stereochemistry. A bold line indicates that a substituent is above the plane of the carbon atom to which it is attached and a dashed line indicates that a substituent is below the plane of the carbon atom to which it is attached.

The term "subject" as used herein is a mammal, e.g., a human, mouse, rat, guinea pig, dog, cat, horse, cow, pig, or non-human primate, such as a monkey, chimpanzee or baboon. In one embodiment, the monkey is a Cynomolgus monkey. In one embodiment, the subject is a human.

The term "treat" is used herein to mean to relieve, reduce or alleviate at least one symptom of a disease in a subject. For example, in relation to eye disorders, the term "treat" may mean to reduce or alleviate intraocular pressure. Within the meaning of the present invention, the term "treat" also denote to arrest, delay the onset (i.e., the period prior to clinical manifestation of a disease) and/or reduce the risk of developing or worsening a disease. The term "protect" is used herein to mean prevent delay or treat, or all, as appropriate, development or continuance or aggravation of a disease in a subject. Within the meaning of the present invention, the eye disorder is associated with an elevated level of intraocular pressure or ocular hypertension. In a particular embodiment, the eye disorder is associated with elevated intraocular pressure.

The term "about" or "approximately" usually refers to within 20%, more preferably within 10%, and most preferably still within 5% of a given value or range. Alternatively, especially in biological systems, the term "about" refers to within about a log (i.e., an order of magnitude) preferably within a factor of two of a given value.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

The following abbreviations are used herein and have the indicated definitions: BSS is balanced salt solution, CCPA is 2-chloro-N6-cyclopentyladenosine; CPA is N6-cyclopentyladenosine; mcg is microgram; mcL is microliter; NECA is adenosine-5'-(N-ethyl)carboxamido; NMR is nuclear magnetic resonance; R-PIA is N6-(2-phenyl-isopropyl)adenosine, R-isomer; OHT is ocular hypertension or POAG is primary open-angle glaucoma.

Administration of the combination includes administration of the combination in a single formulation or unit dosage form, administration of the individual agents of the combination concurrently but separately, or administration of the individual agents of the combination sequentially by any suitable route. The dosage of the individual agents of the combination may require more frequent administration of one of the agents as compared to the other agent in the combination. Therefore, to permit appropriate dosing, packaged pharmaceutical products may contain one or more dosage forms that contain the combination of agents, and one or more dosage forms that contain one of the combinations of agents, but not the other agent(s) of the combination.

Agents may contain one or more asymmetric elements such as stereogenic centers or stereogenic axes, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms; all isomeric forms of the compounds are included in the present invention. In these situations, the single enantiomers (optically active forms) can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

Unless otherwise specified, or clearly indicated by the text, reference to compounds useful in the combination of the invention includes both the free base of the compounds, and all pharmaceutically acceptable salts of the compounds. A preferred dorzolamide salt is the hydrochloride salt. A preferred salt of compound A is the hydrochloride salt. The terms "dorzolamide or its salts," "compound A or its salts" and the like, indicate the pharmaceutically acceptable salts of dorzolamide and compound A, respectively.

Methods of Synthesis

Compounds according to Formula I can be prepared by using synthetic procedures described in U.S. Pat. No. 7,423,144, the disclosure of which is incorporated herein in its entirety.

Modes of Delivery

The combination provided herein can be incorporated into various types of ophthalmic compositions or formulations for delivery. Formula I compounds may be delivered directly to the eye (for example: topical ocular drops or ointments; slow release devices such as pharmaceutical drug delivery sponges implanted in the cul-de-sac or implanted adjacent to the sclera or within the eye; periocular, conjunctival, sub-tenons, intracameral, intravitreal, or intracanalicular injections) or systemically (for example: orally, intravenous, subcutaneous or intramuscular injections; parenterally, dermal or nasal delivery) using techniques well known by those of ordinary skill in the art. It is further contemplated that the agents of the invention may be formulated in intraocular insert or implant devices.

The compounds of Formula I are preferably incorporated into topical ophthalmic formulations with a pH of about 4-8 for delivery to the eye. The compounds may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable surfactant to assist in dissolving the compound. Furthermore, the ophthalmic solution may contain an agent to increase viscosity or solubility such as hydroxypropyl β-Cyclodextrin (HPβCD), hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient may be combined with a preservative in an appropriate vehicle such as mineral oil, liquid lanolin, or white petrolatum. Sterile ophthalmic gel formulations may be prepared by suspending the compound in a hydrophilic base prepared from the combination of, for example, carbopol-974, or the like, according to the published formulations for analogous ophthalmic preparations; preservatives and tonicity agents can be incorporated.

Advantageously, the present invention also provides kits for use by a consumer for treating eye disorders. The invention also provides kits for use by health providers, hospital staff and technicians. The kits can comprise a) a pharmaceutical composition comprising a carbonic anhydrase inhibitor, an adenosine $A_1$ receptor agonist and a pharmaceutically acceptable carrier, vehicle or diluent; and, optionally, b) instructions describing a method of using the pharmaceutical composition for treating the specific disorders. The instructions may also indicate that the kit is for treating disorder while substantially reducing the concomitant liability of adverse effects associated with administration of the composition. In certain embodiments the kits can comprise (i) a carbonic anhydrase inhibitor, with instructions for mixing with (ii) an adenosine $A_1$ receptor agonist, to generate the target combination or active agent for combination therapy.

A "kit" as used in the instant application includes a container for containing the separate unit dosage forms such as an eye dropper, a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

It may be desirable to provide a written memory aid, where the written memory aid is of the type containing information and/or instructions for the physician, pharmacist or subject, e.g., in the form of numbers next to the tablets or capsules whereby the numbers correspond with the days of the regimen which the tablets or capsules so specified should be ingested or a card which contains the same type of information.

Another example of such a memory aid is a calendar printed on the card e.g., as follows "First Week, Monday, Tuesday," . . . etc. . . . "Second Week, Monday, Tuesday, . . . ," etc. Other variations of memory aids will be readily apparent. A "daily dose" can be a single tablet or capsule or several tablets or capsules to be taken on a given day.

Another specific embodiment of a kit is a dispenser designed to dispense the daily doses one at a time. Preferably, the dispenser is equipped with a memory-aid, so as to further facilitate compliance with the regimen. An example of such a memory-aid is a mechanical counter, which indicates the number of daily doses that, has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The following examples illustrate the preparation of certain specific compounds according to the present technology. A skilled artisan appreciates that the invention is not limited to the exemplary work described or to the specific details set forth in the examples.

EXAMPLES

Experimental Procedure

2',3'-Isopropylidene-$N^6$-cyclohexyladenosine

A solution of 6-chloroadenosine (2.58 g) and cyclohexylamine (5 g) in ethanol (20 ml) was heated at reflux for 6 hours then cooled to room temperature. The reaction mixture was concentrated in vacuo and the resultant residue was diluted with water (50 ml) and ethyl acetate (300 ml). The organic layer was separated and the aqueous layer was extracted with ethyl acetate (2×50 ml). The combined organic layers were washed with water (1×30 ml), dried over sodium sulfate, concentrated in vacuo and dried under vacuum to provide $N^6$-cyclohexyladenosine as a white solid (2.600 g). $N^6$-Cyclohexyladenosine (2.6 g) was diluted with acetone (30 ml) and to the resultant solution was added 2,2-dimethoxypropane (12 ml), followed by D-camphorsulphonic acid (3.01 g) and the mixture was allowed to stir at room temperature for 18 hours. The reaction mixture was concentrated in vacuo and the resultant residue was diluted with ethyl acetate (150 ml), then neutralized to pH 8.0 using saturated aqueous NaHCO$_3$. The organic layer was separated, dried over sodium sulfate, concentrated in vacuo. The residue was purified twice on the silica gel column using MeOH—CH$_2$Cl$_2$ (4:96) as an eluent to provide 2',3'-isopropylidene-$N^6$-cyclohexyladenosine (3.16 g). $^1$H NMR (CDCl$_3$): δ 1.23-1.47 (m, 9H), 1.38 (s, 3H), 1.64 (s, 3H), 1.79-1.81 (m, 1H), 2.04-2.06 (m, 1H), 3.80 (d, J=12 Hz, 1H), 3.96 (d, J=12 Hz, 1H), 4.53 (s, 1H), 5.09-5.16 (m, 2H), 5.80-5.92 (m, 2H), 7.79 (s, 1H), 8.24 (s, 1H), 8.22-8.38 (m, 1H).

$N^6$-Cyclohexyladenosine-5'-O-nitrate

Acetic anhydride (6 ml) was slowly added to a stirred solution of nitric acid (2 g, 63%) at −25° C. (CCl$_4$—CO$_2$ bath used for cooling) and the reaction temperature maintained at −7.5 to 0° C. for additional 1 hr. A solution of 2',3'-isopropylidene-$N^6$-cyclohexyladenosine (1.0 g) in acetic anhydride (3 mL) was added slowly. The resultant reaction was allowed to stir at 0 to −5° C. for 2 hour and the mixture was slowly poured slowly into an ice-cold solution of aqueous NaHCO$_3$ (40 mL) and ethyl acetate (150 ml) and it was allowed to stir for 5 minutes. The organic layer was separated and washed with water, dried over sodium sulfate, and concentrated in vacuo. The residue was diluted with a mixture of TFA (16 mL) and water (4 mL) and the mixture was allowed to stir for 30 minutes at room temperature. The mixture was concentrated in vacuo and the resultant residue was diluted with water (10 mL) and concentrated in vacuo. The residue obtained was diluted with ethyl acetate and washed with saturated aqueous sodium bicarbonate, and the organic layer was dried over sodium sulfate and concentrated in vacuo. The residue was purified on the silica gel column using ethyl acetate hexane (from 40:60 to 20:80 gradient) to provide $N^6$-cyclohexyladenosine-5'-O-nitrate (0.150 gm). $^1$H NMR (DMSO-D$_6$): δ 1.08-1.13 (m, 1H), 1.27-1.41 (m, 4H), 1.57-1.83 (m. 6H), 4.12-4.17 (m, 2H), 4.30-4.33 (m, 1H), 5.48 (d, J=5.4 Hz, 1H), 5.60 (d, J=5.7 Hz, 1H), 5.90 (d, J=4.8 Hz, 1H), 7.59 (d, J=8.1 Hz, 1H), 8.16 (s, 1H), 8.29 (s, 1H).

$N^6$-(exo-2-Norbornyl)adenosine-5'-O-nitrate

2',3'-Isopropylidene-$N^6$-exo-norbornyladenosine was prepared following the procedure of 2',3'-isopropylidene-$N^6$-cyclohexyladenosine and used for the subsequent reaction. Acetic anhydride (6 ml) was slowly added to a stirred solution of nitric acid (2 g, 63%) at −25° C. (CCl$_4$-0O$_2$ bath used for cooling) and the reaction temperature maintained at −7.5 to 0° C. for additional 1 hr. A solution of 2',3'-isopropylidene-$N^6$-exo-norbornyladenosine (1.2 g) in acetic anhydride (3 mL) was added slowly. The mixture was allowed to stir at 0 to −5° C. for 40 minutes and the mixture was slowly poured slowly into an ice-cold solution of aqueous NaHCO$_3$ (40 mL). The solution was extracted in dichloromethane. The organic layer was separated and washed with brine, dried over sodium sulfate, and concentrated under vacuo. The residue was purified on the silica gel column using ethyl acetate-hexane (1:1) to provide the desired product (0.245 g) and the starting compound (1.0 g). The nitro product (0.245 g) was diluted in a mixture of TFA (15 mL) and water (5 mL) and the mixture was allowed to stir for 30 minutes at room temperature. It was concentrated under vacuo and diluted with water (10 mL) and concentrated in vacuo. The resultant residue was diluted with ethyl acetate and washed with saturated aqueous sodium bicarbonate. The organic layer was dried over sodium sulfate and concentrated in vacuo. The residue was recrystallized from the mixture of ethyl acetate and hexane to provide $N^6$-exo-2-norbornyladenosine-5'-O-nitrate (0.123 gm). $^1$H NMR (DMSO-D$_6$): δ 1.03-1.21 (m, 3H), 1.40-1.56 (m, 3H), 1.58-1.64 (m. 4H), 3.94 (bs, 1H), 4.13-4.17 (m, 1H), 4.30 (bs, 1H), 4.66-4.87 (m, 3H), 5.49 (d, J=5.4 Hz, 1H), 5.62 (d, J=5.4 Hz, 1H), 5.91 (d, J=4.8 Hz, 1H), 7.60 (d, J=6.6 Hz, 1H), 8.20 (s, 1H), 8.31 (s, 1H).

Recently conducted pre-clinical studies show that the use of a combination of dorzolamide and an adenosine A$_1$ receptor agonist, specifically Compound A and dorzolamide provided significant IOP reduction in normotensive monkeys.

The experiments were conducted in ten conscious cynomolgus monkeys (*Macaca fascicularis*). The monkeys were without ocular disease and had intraocular pressure readings in the normal range, and were classed as normotensive monkeys. Prior to the study, the monkeys were previously acclimated to the study procedures (e.g., dosing, tonometry, ocular examinations, and handling), and allowed a washout period before each treatment.

Compound A was administered using the following aqueous suspension formulation:

Aqueous Suspension Formulation
The aqueous formulation comprised of the following:

| Ingredient | %, w/v |
| --- | --- |
| Compound A, micronized | 2.0 |
| Sodium CMC, low viscosity | 0.7 |
| Benzalkonium Chloride | 0.01 |
| Polysorbate 80 | 0.3 |
| Citric Acid Monohydrate | 0.15 (7 mM) |
| NaCl | 0.8% (qs to 290-300 mOsm) |
| NaOH/HCl (pH adjustment) | pH 5.1 ± 0.1 |
| Purified Water | q.s. 100 |

Treatment 1

In the first treatment, 10 monkeys received topically 100 mcg of Compound A at 40 mcL, formulated in an aqueous suspension in one study eye and placebo control applied topically in the contralateral eye. During the study, the intraocular pressures (IOP) of both the treated and control eyes were measured repeatedly using a calibrated pneumatonometer. The control in the first treatment was a 40 mcL composition of 0.8% sodium chloride (NaCl), 0.15% citrate, 0.01% benzalkonium chloride, 0.3% polysorbate 80, and 0.7% sodium (Na) carboxymethylcellulose.

Treatment 2

In the second treatment, 20 monkeys received dorzolamide (Trusopt™) dosed via 2 drops (at a concentration of 2%) for a total dose of 1000 mcg in one study eye and 2 drops of balanced salt solution (BSS) vehicle in the contralateral eye as the control. The IOPs of both eyes were measured repeatedly using a calibrated pneumatonometer over a period of 8 hours after dosing.

Treatment 3

In the third treatment, 10 monkeys received dorzolamide (Trusopt™) topically dosed via 2 drops (at a concentration of 2%) for a total dose of 1000 mcg in one study eye and immediately after the monkeys received the additional topical dose of 100 mcg of Compound A at 40 mcL formulated in an aqueous suspension in the same study eye and BSS vehicle and placebo of 0.8% sodium chloride (NaCl), 0.15% citrate, 0.01% benzalkonium chloride, 0.3% polysorbate 80, and 0.7% sodium (Na) carboxymethylcellulose topically in the contralateral eye. The dorzolamide and Compound A were given approximately 5 minutes apart. The IOPs of both eyes were measured repeatedly using a calibrated pneumatonometer.

Results

Figure 2:
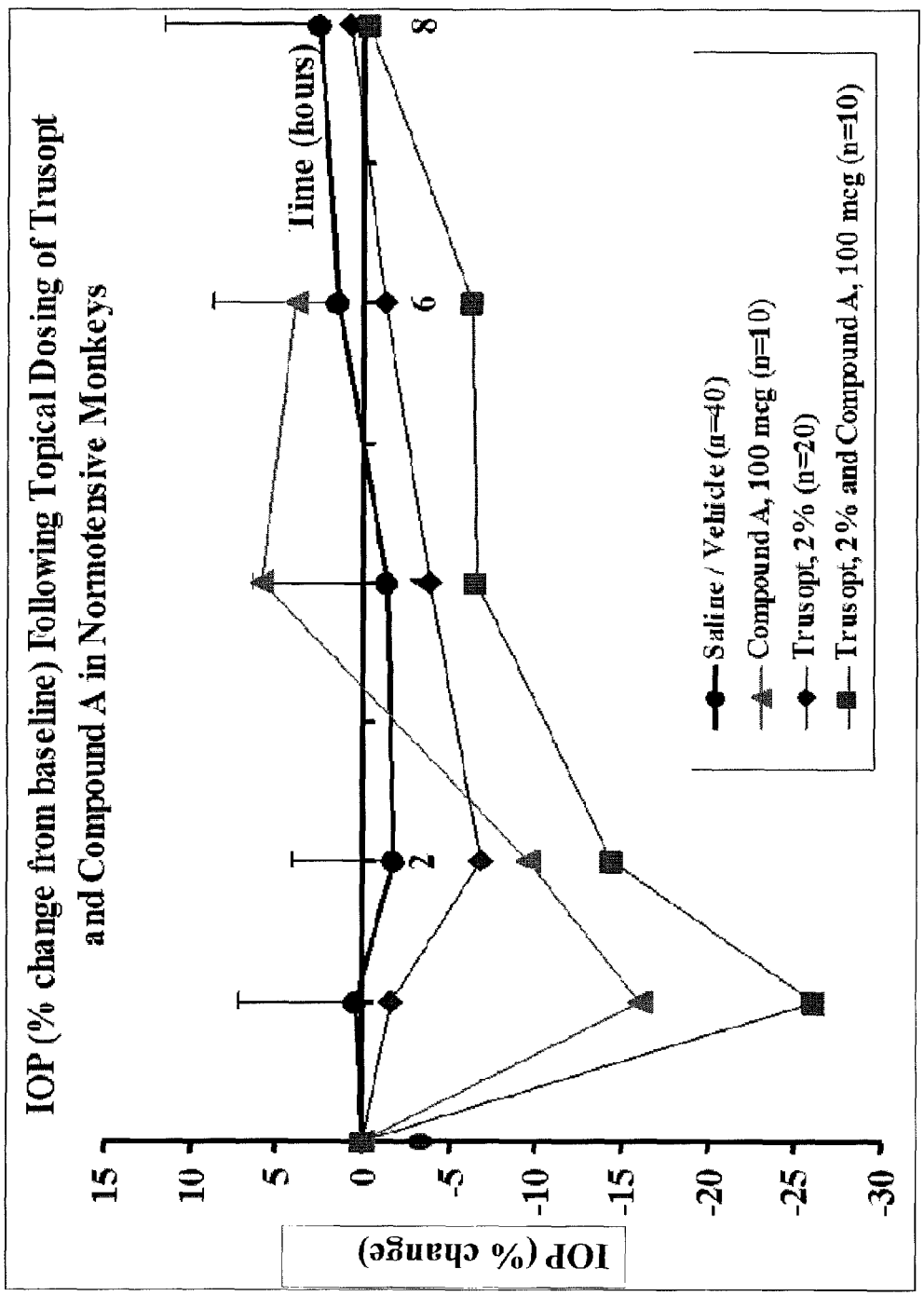
FIG. 2: shows a plot over 8 hrs of the reduction in IOP (% change from baseline) in normotensive monkeys following ocular dosing of 100 mcg of Compound A alone at 0 hrs, and ocular dosing of a carbonic anhydrase inhibitor (Trusopt, 2%) alone at 0 hrs compared to the reduction in IOP following ocular dosing of both 100 mcg of Compound A and a carbonic anhydrase inhibitor (Trusopt, 2%) at 0 hrs.

The results from the treatments are illustrated in FIGS. 1 and 2. The plots in FIGS. 1 and 2 show the reduction of IOP in (mmHg and % change from baseline) following the combination ocular dosing of 100 mcg of a suspension of Compound A and 2% of Trusopt™ relative to the reduction of IOP seen with the ocular dosing 100 mcg of Compound A or 2% of Trusopt™ alone.

It is anticipated by the Applicant that results of a similar or more significant extent would be observed similarly to other mammals including humans with glaucoma, POAG or OHT.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to combinations, kits, compounds, means, methods, and/or steps disclosed herein.

The invention claimed is:

1. An ophthalmic composition comprising
i) an adenosine $A_1$ receptor agonist compound of formula (I),

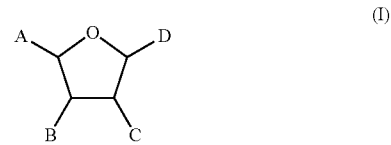

or pharmaceutically acceptable salts thereof;
wherein
A is —$CH_2OH$, —$(CH_2)_nONO_2$, —$CH_2OSO_3Na$ or —$CH_2OSO_3H$; wherein n=1-6;
B and C are —OH;
D is

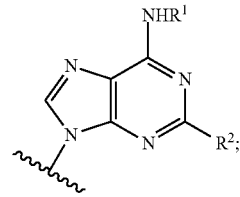

A and B are trans with respect to each other;
B and C are cis with respect to each other;
C and D are cis or trans with respect to each other;
$R^1$ is —H, —$C_1$-$C_{10}$ alkyl, -aryl, -3- to 7-membered monocyclic heterocyclyl, -8- to 12-membered bicyclic heterocyclyl, —$C_3$-$C_8$ monocyclic cycloalkyl, —$C_3$-$C_8$ monocyclic cycloalkenyl, —$C_8$-$C_{12}$ bicyclic cycloalkyl, —$C_8$-$C_{12}$ bicyclic cycloalkenyl —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), or —$(CH_2)_n$-aryl;
$R^2$ is —H, halo, —CN, —$NHR^4$, —$NHC(O)R^4$, —$NHC(O)OR^4$, —$NHC(O)NHR^4$, —$NHNHC(O)R^4$, —$NHNHC(O)OR^4$, —$NHNHC(O)NHR^4$, or —NH—N=$C(R^6)R^7$;
$R^4$ is —$C_1$-$C_{15}$ alkyl, -aryl, —$(CH_2)_n$-aryl, —$(CH_2)_n$-(3- to 7-membered monocyclic heterocyclyl), —$(CH_2)_n$-(8- to 12-membered bicyclic heterocyclyl), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —C≡C—($C_1$-$C_{10}$ alkyl) or —C≡C-aryl;

R⁶ is —C₁-C₁₀ alkyl, -aryl, —(CH₂)ₙ-aryl, —(CH₂)ₙ-(3- to 7-membered monocyclic heterocyclyl), —(CH₂)ₙ-(8- to 12-membered bicyclic heterocyclyl), —(CH₂)ₙ—(C₃-C₈ monocyclic cycloalkyl), —(CH₂)ₙ—(C₃-C₈ monocyclic cycloalkenyl), —(CH₂)ₙ—(C₈-C₁₂ bicyclic cycloalkyl), —(CH₂)ₙ—(C₈-C₁₂ bicyclic cycloalkenyl), —(CH₂)ₙ—(C₃-C₈ monocyclic cycloalkenyl), -phenylene-(CH₂)ₙCOOH, or -phenylene-(CH₂)ₙCOO—(C₁-C₁₀ alkyl);

R⁷ is —H, —C₁-C₁₀ alkyl, -aryl, —(CH₂)ₙ-aryl, —(CH₂)ₙ-(3- to 7-membered monocyclic heterocyclyl), —(CH₂)ₙ-(8- to 12-membered bicyclic heterocyclyl), —(CH₂)ₙ—(C₃-C₈ monocyclic cycloalkyl), —(CH₂)ₙ—(C₃-C₈ monocyclic cycloalkenyl), —(CH₂)ₙ—(C₈-C₁₂ bicyclic cycloalkenyl) or —(CH₂)ₙ—(C₈-C₁₂ bicyclic cycloalkyl) and each n is independently an integer ranging from 1 to 5, wherein -3- to 7-membered monocyclic heterocyclyl is a 3- or 4-membered non-aromatic monocyclic cycloalkyl in which 1 of the ring carbon atoms has been replaced with an N, O or S atom; or a 5-, 6-, or 7-membered aromatic or non-aromatic monocyclic cycloalkyl in which 1-4 of the ring carbon atoms have been independently replaced with a N, O or S atom, wherein -8- to 12-membered bicyclic heterocyclyl is a bicyclic 8- to 12-membered aromatic or non-aromatic bicyclic cycloalkyl in which one or both of the rings of the bicyclic ring system have 1-4 of its ring carbon atoms independently replaced with a N, O or S atom, and ii) a carbonic anhydrase inhibitor.

2. The composition according to claim 1 wherein the carbonic anhydrase inhibitor is selected from the group consisting of dorzolamide, brinzolamide and acetazolamide.

3. The composition according to claim 1 wherein the carbonic anhydrase inhibitor is dorzolamide.

4. The composition according to claim 1,
wherein
A is —(CH₂)ₙONO₂;
R¹ is –3- to 7-membered monocyclic heterocyclyl, —C₃-C₈ monocyclic cycloalkyl, or —C₈-C₁₂ bicyclic cycloalkyl;
R² is —H or halo; and
C and D are trans with respect to each other.

5. The composition according to claim 4,
wherein
R¹ is —C₃-C₈ monocyclic cycloalkyl; and
R² is —H.

6. The composition according to claim 4,
wherein
n is 1.

7. The composition according to claim 1 wherein the compound of Formula I is selected from the group consisting of:

Compound A ((2R,3S,4R,5R)-5-(6-(cyclopentylamino)-9H-purin-9-yl)-3,4-dihydroxytetrahydrofuran-2-yl)methyl nitrate, Compound B ((2R,3S,4R,5R)-5-(2-chloro-6-(cyclopentylamino)-9H-purin-9-yl)-3,4-dihydroxytetrahydrofuran-2-yl)methyl nitrate, Compound C sodium((2R,3S,4R,5R)-5-(6-(cyclopentylamino)-9H-purin-9-yl)-3,4-dihydroxytetrahydrofuran-2-yl)methyl sulfate, Compound D

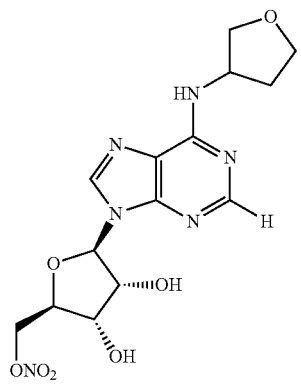

((2R,3S,4R,5R)-3,4-dihydroxy-5-(6-(tetrahydrofuran-3-ylamino)-9H-purin-9-yl)tetrahydrofuran-2-yl)methyl nitrate, Compound E

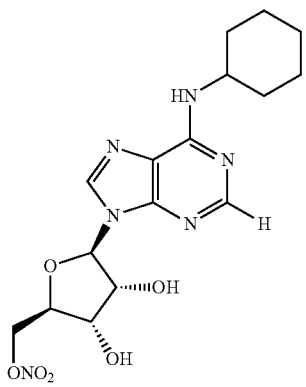

((2R,3S,4R,5R)-5-(6-(cyclohexylamino)-9H-purin-9-yl)-3,4-dihydroxytetrahydrofuran-2-yl)methyl nitrate, Compound F

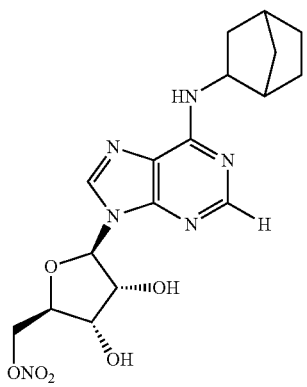

((2R,3S,4R,5R)-5-(6-(bicycle-[2.2.1]-heptan-2-ylamino)-9H-purin-9-yl)-3,4-dihydroxytetrahydrofuran-2-yl)methyl nitrate, Compound G

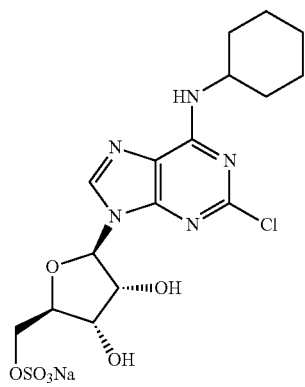

sodium((2R,3S,4R,5R)-5-(2-chloro-6-(cyclohexylamino)-9H-purin-9-yl)-3,4-dihydroxytetrahydrofuran-2-yl)methyl sulfate, Compound H

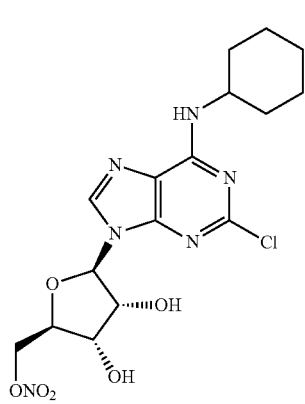

((2R,3S,4R,5R)-5-(2-chloro-6-(cyclohexylamino)-9H-purin-9-yl)-3,4-dihydroxytetrahydrofuran-2-yl)methyl nitrate Compound I

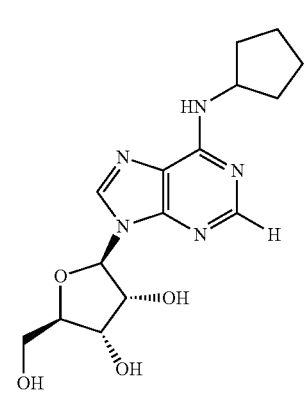

(2R,3R,4S,5R)-2-(6-(cyclopentylamino)-9H-purin-9-yl)-5-(hydroxymethyl)tetrahydrofuran-3,4-diol (N$^6$-cyclopentyl adenosine (CPA)), and

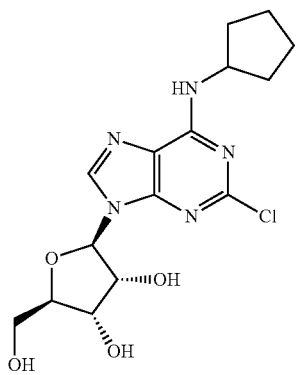

Compound J (2R,3R,4S,5R)-2-(2-chloro-6-(cyclopentylamino)-9H-purin-9-yl)-5-(hydroxymethyl)tetrahydrofuran-3,4-diol (2-chloro-$N^6$-cyclopentyl adenosine (CCPA)); or pharmaceutically acceptable salts thereof.

8. The composition according to claim 1 wherein the adenosine $A_1$ agonist is Compound A, ((2R,3S,4R,5R)-5-(6-(cyclopentylamino)-9H-purin-9-yl)-3,4-dihydroxytetrahydrofuran-2-yl)methyl nitrate or a pharmaceutically acceptable salt thereof.

9. An ophthalmic pharmaceutical composition comprising dorzolamide, an adenosine $A_1$ receptor agonist according to claim 1, and a pharmaceutically acceptable vehicle or excipient.

10. The pharmaceutical composition of claim 9, wherein the pharmaceutically acceptable vehicle or excipient is selected from the group consisting of: ophthalmologically acceptable preservatives, surfactants, viscosity enhancers, penetration enhancers, gelling agents, hydrophobic bases, vehicles, buffers, sodium chloride, and water, or any combination thereof.

11. A kit comprising
i) an adenosine $A_1$ receptor agonist compound of formula (I),

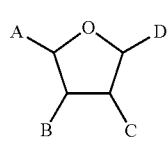

(I)

or pharmaceutically acceptable salts thereof; wherein
A is —CH$_2$OH, —(CH$_2$)$_n$ONO$_2$, —CH$_2$OSO$_3$Na or —CH$_2$OSO$_3$H; wherein n=1-6;
B and C are —OH;
D is

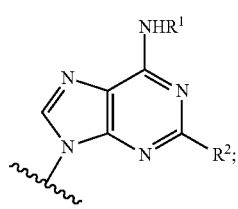

A and B are trans with respect to each other;

B and C are cis with respect to each other;

C and D are cis or trans with respect to each other;

$R^1$ is —H, —C$_1$-C$_{10}$ alkyl, -aryl, -3- to 7-membered monocyclic heterocyclyl, -8- to 12-membered bicyclic heterocyclyl, —C$_3$-C$_8$ monocyclic cycloalkyl, —C$_3$-C$_8$ monocyclic cycloalkenyl, —C$_8$-C$_{12}$ bicyclic cycloalkyl, —C$_8$-C$_{12}$ bicyclic cycloalkenyl —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), or —(CH$_2$)$_n$-aryl;

$R^2$ is —H, halo, —CN, —NHR$^4$, —NHC(O)R$^4$, —NHC(O)OR$^4$, —NHC(O)NHR$^4$, —NHNHC(O)R$^4$, —NHNHC(O)OR$^4$, —NHNHC(O)NHR$^4$, or —NH—N=C(R$^6$)R$^7$;

$R^4$ is —C$_1$-C$_{15}$ alkyl, -aryl, —(CH$_2$)$_n$-(3- to 7-membered monocyclic heterocyclyl), —(CH$_2$)$_n$-(8- to 12-membered bicyclic heterocyclyl), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —C≡C—(C$_1$-C$_{10}$ alkyl) or —C≡C-aryl;

$R^6$ is —C$_1$-C$_{10}$ alkyl, -aryl, —(CH$_2$)$_n$-(3- to 7-membered monocyclic heterocyclyl), —(CH$_2$)$_n$-(8- to 12-membered bicyclic heterocyclyl), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkyl), —(CH$_2$)$_n$—(C$_8$-C$_{12}$ bicyclic cycloalkenyl), —(CH$_2$)$_n$—(C$_3$-C$_8$ monocyclic cycloalkenyl), -phenylene-(CH$_2$)$_n$COOH, or -phenylene-(CH$_2$)$_n$COO—(C$_1$-C$_{10}$ alkyl);

$R^7$ is —H, —C$_1$-C$_{10}$ alkyl, -aryl, —(CH$_2$)$_n$-aryl, —(CH$_2$)$_n$-(3- to 7-membered monocyclic heterocyclyl), —(CH$_2$)$_n$-(8- to 12-membered bicyclic heterocyclyl), —(CH$_2$)$_n$—(C$_3$-C$_8$ monocyclic cycloalkyl), —(CH$_2$)$_n$—(C$_3$-C$_8$ monocyclic cycloalkenyl), —(CH$_2$)$_n$—(C$_8$-C$_{12}$ bicyclic cycloalkenyl) or —(CH$_2$)$_n$—(C$_8$-C$_{12}$ bicyclic cycloalkyl) and each n is independently an integer ranging from 1 to 5, wherein -3- to 7-membered monocyclic heterocyclyl is a 3- or 4-membered non-aromatic monocyclic cycloalkyl in which 1 of the ring carbon atoms has been replaced with an N, O or S atom; or a 5-, 6-, or 7-membered aromatic or non-aromatic monocyclic cycloalkyl in which 1-4 of the ring carbon atoms have been independently replaced with a N, O or S atom, wherein -8- to 12-membered bicyclic heterocyclyl is a bicyclic 8- to 12-membered aromatic or non-aromatic bicyclic cycloalkyl in which one or both of the rings of the bicyclic ring system have 1-4 of its ring carbon atoms independently replaced with a N, O or S atom, and ii) a carbonic anhydrase inhibitor.

12. The kit according to claim 11, wherein the carbonic anhydrase inhibitor is selected from the group consisting of dorzolamide, brinzolamide and acetazolamide.

13. The kit according to claim 11, wherein the carbonic anhydrase inhibitor is dorzolamide.

14. The kit according to claim 11, wherein the compound of Formula I is selected from the group consisting of:

Compound A

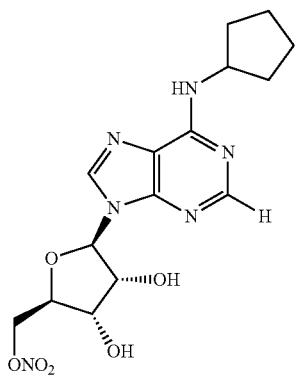

((2R,3S,4R,5R)-5-(6-(cyclopentylamino)-9H-purin-9-yl)-3,4-dihydroxytetrahydrofuran-2-yl)methyl nitrate, Compound B

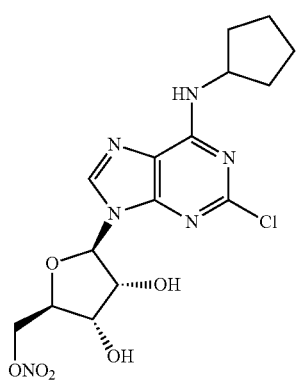

((2R,3S,4R,5R)-5-(2-chloro-6-(cyclopentylamino)-9H-purin-9-yl)-3,4-dihydroxytetrahydrofuran-2-yl)methyl nitrate, Compound C

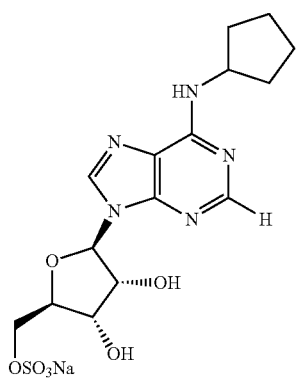

sodium((2R,3S,4R,5R)-5-(6-(cyclopentylamino)-9H-purin-9-yl)-3,4-dihydroxytetrahydrofuran-2-yl)methyl sulfate, Compound D

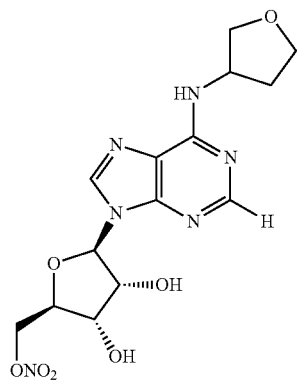

((2R,3S,4R,5R)-3,4-dihydroxy-5-(6-(tetrahydrofuran-3-ylamino)-9H-purin-9-yl)tetrahydrofuran-2-yl)methyl nitrate, Compound E

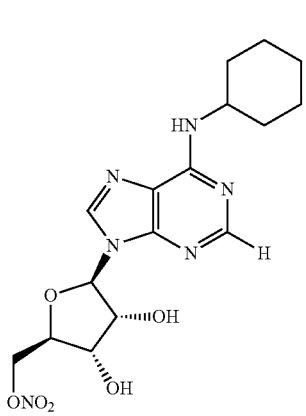

((2R,3S,4R,5R)-5-(6-(cyclohexylamino)-9H-purin-9-yl)-3,4-dihydroxytetrahydrofuran-2-yl)methyl nitrate, Compound F

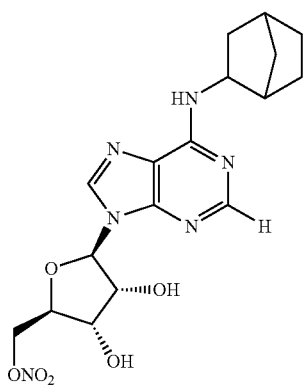

((2R,3S,4R,5R)-5-(6-(bicycle-[2.2.1]-heptan-2-ylamino)-9H-purin-9-yl)-3,4-dihydroxytetrahydrofuran-2-yl)methyl nitrate, Compound G

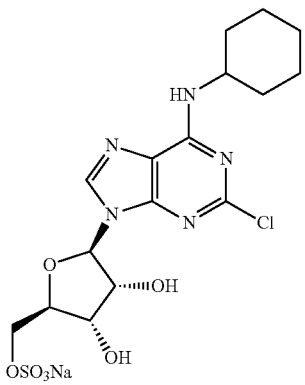

sodium((2R,3S,4R,5R)-5-(2-chloro-6-(cyclohexy-
  lamino)-9H-purin-9-yl)-3,4-dihydroxytetrahydrofuran-
  2-yl)methyl sulfate, Compound H

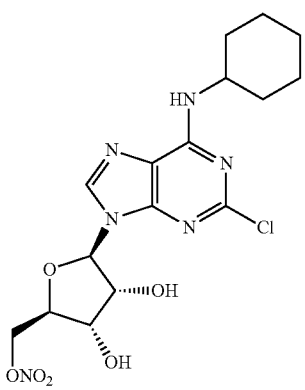

((2R,3S,4R,5R)-5-(2-chloro-6-(cyclohexylamino)-9H-
  purin-9-yl)-3,4-dihydroxytetrahydrofuran-2-yl)methyl
  nitrate Compound I

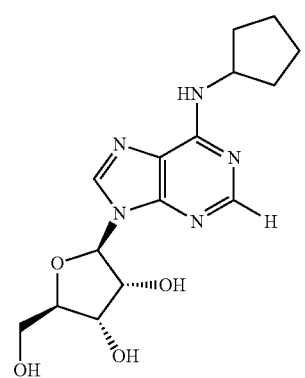

(2R,3R,4S,5R)-2-(6-(cyclopentylamino)-9H-purin-9-yl)-
  5-(hydroxymethyl)tetrahydrofuran-3,4-diol ($N^6$-cyclo-
  pentyl adenosine (CPA)), and Compound J

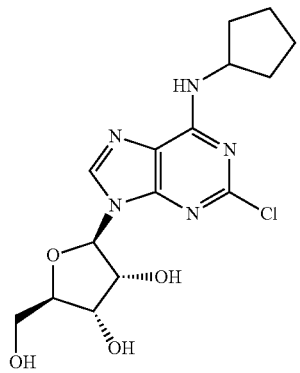

(2R,3R,4S,5R)-2-(2-chloro-6-(cyclopentylamino)-9H-
  purin-9-yl)-5-(hydroxymethyl)tetrahydrofuran-3,4-
  diol (2-chloro-$N^6$-cyclopentyl adenosine (CCPA));
or pharmaceutically acceptable salts thereof.

15. The kit according to claim 11, wherein the adenosine $A_1$ agonist is Compound A, ((2R,3S,4R,5R)-5-(6-(cyclopentylamino)-9H-purin-9-yl)-3,4-dihydroxytetrahydrofuran-2-yl)methyl nitrate or a pharmaceutically acceptable salt thereof.

16. An ophthalmic composition comprising ((2R,3S,4R,5R)-5-(6-(cyclopentylamino)-9H-purin-9-yl)-3,4-dihydroxytetrahydrofuran-2-yl)methyl nitrate and dorzolamide or pharmaceutically acceptable salts thereof.

17. A method of treating an eye disorder in a subject, comprising administering to an eye of the subject in need thereof, an effective amount of i) an adenosine $A_1$ receptor agonist compound of formula (I),

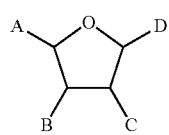

(I)

or pharmaceutically acceptable salts thereof;
wherein
  A is —CH$_2$OH, —(CH$_2$)$_n$ONO$_2$, or —CH$_2$OSO$_3$H;
    wherein n=1-6;
  B and C are —OH;
  D is

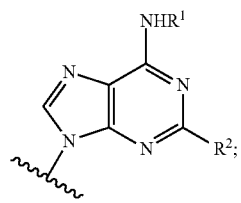

A and B are trans with respect to each other;
  B and C are cis with respect to each other;
  C and D are cis or trans with respect to each other;
  R$^1$ is —H, —C$_1$-C$_{10}$ alkyl, -aryl, -3- to 7-membered monocyclic heterocyclyl, -8- to 12-membered bicyclic heterocyclyl, —C$_3$-C$_8$ monocyclic cycloalkyl, —C$_3$-C$_8$ monocyclic cycloalkenyl, —C$_8$-C$_{12}$ bicyclic cycloalkyl, —$C_8$-$C_{12}$ bicyclic cycloalkenyl —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$ —($C_8$-$C_{12}$ bicyclic cycloalkenyl), or —$(CH_2)_n$-aryl;

$R^2$ is —H, halo, —CN, —$NHR^4$, —$NHC(O)R^4$, —$NHC(O)OR^4$, —$NHC(O)NHR^4$, —$NHNHC(O)R^4$, —$NHNHC(O)OR^4$, —$NHNHC(O)NHR^4$, or —NH—N=C($R^6$)$R^7$;

$R^4$ is —$C_1$-$C_{15}$ alkyl, -aryl, —$(CH_2)_n$-aryl, —$(CH_2)_n$-(3- to 7-membered monocyclic heterocyclyl), —$(CH_2)_n$-(8- to 12-membered bicyclic heterocyclyl), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$ —($C_8$-$C_{12}$ bicyclic cycloalkenyl), —C≡C—($C_1$-$C_{10}$ alkyl) or —C≡C-aryl;

$R^6$ is —$C_1$-$C_{10}$ alkyl, -aryl, —$(CH_2)_n$-aryl, —$(CH_2)_n$-(3- to 7-membered monocyclic heterocyclyl), —$(CH_2)_n$-(8- to 12-membered bicyclic heterocyclyl), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$ —($C_8$-$C_{12}$ bicyclic cycloalkenyl), —$(CH_2)_n$—($C_3$-$C_8$ monocyclic cycloalkenyl), -phenylene-$(CH_2)_n$ COOH, or -phenylene-$(CH_2)_n$COO—($C_1$-$C_{10}$ alkyl);

$R^7$ is —H, —$C_1$-$C_{10}$ alkyl, -aryl, —$(CH_2)_n$-aryl, —$(CH_2)_n$-(3- to 7-membered monocyclic heterocyclyl), —$(CH_2)_n$-(8- to 12-membered bicyclic heterocyclyl), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkenyl) or —$(CH_2)_n$—($C_8$-$C_{12}$ bicyclic cycloalkyl) and each n is independently an integer ranging from 1 to 5, wherein -3- to 7-membered monocyclic heterocyclyl is a 3- or 4-membered non-aromatic monocyclic cycloalkyl in which 1 of the ring carbon atoms has been replaced with an N, O or S atom; or a 5-, 6-, or 7-membered aromatic or non-aromatic monocyclic cycloalkyl in which 1-4 of the ring carbon atoms have been independently replaced with a N, O or S atom, wherein -8- to 12-membered bicyclic heterocyclyl is a bicyclic 8- to 12-membered aromatic or non-aromatic bicyclic cycloalkyl in which one or both of the rings of the bicyclic ring system have 1-4 of its ring carbon atoms independently replaced with a N, O or S atom, and ii) a carbonic anhydrase inhibitor or pharmaceutically acceptable salts thereof.

18. The method according to claim 17, wherein the eye disorder is elevated intraocular pressure.

19. The method according to claim 17 wherein the $A_1$ receptor agonist compound is applied to an eye of the subject in need thereof, simultaneously, separately or sequentially to the application of the carbonic anhydrase inhibitor to the eye of the subject.

20. The method according to claim 17 wherein the $A_1$ receptor agonist compound is applied to an eye of the subject in need thereof, simultaneously to the application of the carbonic anhydrase inhibitor to the eye of the subject.

21. The method according to claim 17 wherein the $A_1$ receptor agonist compound is applied to an eye of the subject in need thereof, sequentially to the application of the carbonic anhydrase inhibitor to the eye of the subject.

22. The method according to claim 17, further comprising applying about 0.05 mg/ml to about 7.0 mg/ml of the $A_1$ receptor agonist compound with about 2% of a carbonic anhydrase inhibitor to an eye of the subject in need thereof, from 1 to 4 times daily.

23. The method according to claim 17, further comprising applying about 20-700 μg of the $A_1$ receptor agonist compound to an eye of the subject in need thereof, from 1 to 2 times daily.

24. The method according to claim 17, further comprising applying about 20-350 μg of the $A_1$ receptor agonist compound to an eye of the subject in need thereof, from 1 to 2 times daily.

25. The method according to claim 17, wherein the $A_1$ receptor agonist compound and the carbonic anhydrase inhibitor are administered topically as one or more eye drops to the eye of the subject in need thereof.

26. A method of reducing intraocular pressure (IOP) and associated diseases and conditions caused by elevated IOP in a subject comprising administering an effective amount of a composition according to claim 1 to an affected eye of the subject in need thereof.

27. The method according to claim 26, wherein the diseases and conditions caused by elevated IOP in the subject are selected from the group consisting of normal-tension glaucoma, ocular hypertension (OHT), and primary open-angle glaucoma (POAG).

28. A method of treating an eye disorder in a subject, comprising administering to an eye of the subject in need thereof, an effective amount of ((2R,3S,4R,5R)-5-(6-(cyclopentylamino)-9H-purin-9-yl)-3,4-dihydroxytetrahydrofuran-2-yl)methyl nitrate and dorzolamide or pharmaceutically acceptable salts thereof.

29. The method of claim 28, wherein the eye disorder is elevated intraocular pressure.

30. The method according to claim 28 wherein ((2R,3S,4R,5R)-5-(6-(cyclopentylamino)-9H-purin-9-yl)-3,4-dihydroxytetrahydrofuran-2-yl)methyl nitrate is applied to an eye of the subject in need thereof, simultaneously to the application of dorzolamide to the eye of the subject.

31. The method according to claim 28 wherein ((2R,3S,4R,5R)-5-(6-(cyclopentylamino)-9H-purin-9-yl)-3,4-dihydroxytetrahydrofuran-2-yl)methyl nitrate is applied to an eye of the subject in need thereof, sequentially to the application of dorzolamide to the eye of the subject.

* * * * *

UNITED STATES PATENT AND TRADEMARK OFFICE
CERTIFICATE OF CORRECTION

PATENT NO. : 8,440,639 B2  
APPLICATION NO. : 13/051633  
DATED : May 14, 2013  
INVENTOR(S) : Norman N. Kim et al.

It is certified that error appears in the above-identified patent and that said Letters Patent is hereby corrected as shown below:

In the Claims

Column 30, claim 11, line 18, should read:

$R^4$ is $-C_1-C_{15}$ alkyl, - aryl, $-(CH_2)_n$-aryl, $-(CH_2)_n$-(3- to 7-mem- Column 30, claim 11, line 26, should read:

$R^6$ is $-C_1-C_{10}$ alkyl, - aryl, $-(CH_2)_n$-aryl, $-(CH_2)_n$-(3- to 7-mem- Signed and Sealed this  
First Day of July, 2014

Michelle K. Lee  
*Deputy Director of the United States Patent and Trademark Office*